United States Patent

Takahashi et al.

Patent Number: 5,893,559
Date of Patent: Apr. 13, 1999

[54] APPARATUS FOR SAMPLING A SMALL NUMBER OF PRINTED SHEETS FROM PRINTED SHEETS CONVEYANCE LINE

[75] Inventors: Tohri Takahashi; Yoshio Ikeda, both of Yokohama; Ryuichi Satoh, Kawasaki, all of Japan

[73] Assignee: Tokyo Kikai Seisakusho, Ltd., Tokyo, Japan

[21] Appl. No.: 09/022,895

[22] Filed: Feb. 12, 1998

[30] Foreign Application Priority Data

Jun. 9, 1997 [JP] Japan ................... 9-164949

[51] Int. Cl.$^6$ .............. B65H 29/44; G01N 1/00; B65G 37/00
[52] U.S. Cl. .............. 271/280; 73/863.91; 198/358
[58] Field of Search .................. 271/3.19, 225, 271/280, 285, 286, 177, 180, 184, 188, 265.03, 261, 227; 198/370.07; 73/863.91, 863.92

[56] References Cited

U.S. PATENT DOCUMENTS

| | | | |
|---|---|---|---|
| 4,072,060 | 2/1978 | Kitai et al. | 73/423 |
| 4,338,671 | 7/1982 | Korytkowski et al. | 364/478 X |
| 5,322,012 | 6/1994 | Gartner et al. | 271/227 |
| 5,647,589 | 7/1997 | Kurandt | 271/280 |

FOREIGN PATENT DOCUMENTS

| | | |
|---|---|---|
| 55-5466 | 2/1980 | Japan . |
| 55-31069 | 8/1980 | Japan . |
| 55-31070 | 8/1980 | Japan . |

*Primary Examiner*—H. Grant Skaggs
*Assistant Examiner*—Kenneth W. Bower
*Attorney, Agent, or Firm*—Armstrong, Westerman, Hattori, McLeland & Naughton

[57] ABSTRACT

A sampling apparatus automatically samples a small number of printed sheets from a conveyance path which is formed by two opposed conveyance members constituting the conveyance path and through which folded printed sheets are conveyed in a line and overlap each other at a certain pitch. The sampled printed sheets are taken out from the conveyance path through an opening portion formed in one of the conveyance members. The apparatus includes a sample plate. The sampling plate reciprocates linearly between a wait position and an advanced position. When the sampling plate is advanced, the sampling plate traverse a conveyance path zone corresponding to the opening portion and reaches the opening portion, while maintaining a posture in which the sampling plate is substantially parallel to the printed sheets line. When the sampling plate is retracted, the sample plate changes its posture to a second posture in which the sampling plate is substantially perpendicular to the printed sheets line and situated outside a side edge of the printed sheets line in order to avoid interference with the printed sheets line during its retreat. When the sampling plate is temporarily stopped in the conveyance path zone during the advancement, a capture portion of the sampling plate blocks the conveyance of printed sheets to be sampled and separates them from the printed sheets line for ejection.

16 Claims, 7 Drawing Sheets

APPARATUS FOR SAMPLING A SMALL NUMBER OF PRINTED SHEETS FROM PRINTED SHEETS CONVEYANCE LINE

BACKGROUND OF THE INVENTION

1. Field of the Invention

The present invention relates to an apparatus for sampling, for quality inspection purposes, a small number of printed sheets (e.g. 2 printed sheets) from a printed sheets line in a conveyance path along which folded printed sheets are conveyed to a counter stacker or the like in a line overlapping each other at certain pitches.

2. Description of the Related Art

Conventional apparatuses for sampling a small number of printed sheets from a printed sheets conveyance line are disclosed in, for example, Japanese Patent Publication (kokoku) Nos. 55-31070, 55-31069, and 55-5466.

The apparatus disclosed in Japanese Patent Publication No. 55-31070 includes: an opening portion formed on one side of the rising section of a conveyance path for conveying printed sheets from the folder unit of a rotary press to a counter stacker or the like; a sampling plate located in the vicinity of the conveyance path and angularly displaced by first driving means to thereby advance into the conveyance path from behind the opening portion; a capture portion located at the tip portion of the sampling plate for capturing a small number of printed sheets from a line of printed sheets conveyed along the conveyance path when the sampling plate advances into the conveyance path; an ejection palate located opposite the sampling plate with respect to the conveyance path for ejecting the sampled printed sheets onto a receiver; and second driving means for angularly displacing the sampling plate beyond the side of the printed sheets line after completion of the sampling.

In the apparatus, the sampling plate stands by in the vicinity of a line of printed sheets, which are conveyed from the folder unit of the rotary press and overlap each other at certain pitches. In response to a manually issued sampling instruction, the sampling plate is angularly moved by the first driving means via a driving shaft to thereby advance into the printed sheets line. Thus, when the leading ends of a small number of printed sheets enter the capture portion, advancement of the printed sheets is prevented. Subsequently, the captured printed sheets are separated from the printed sheets line.

The thus-sampled printed sheets stand stationary in a curved shape. Meanwhile, when the sampling plate advances into the printed sheets line, a limit switch goes ON to generate an electric signal. The electric signal triggers the counting of pulses of an electric pulse signal output at a rate corresponding to the printing speed of the rotary press. When the number of counted pulses reaches a preset pulse number—which corresponds to a travel distance of the printed sheets equal to a length of a single printed sheet, a counting end signal is issued. In response to the counting end signal, the sampling plate is angularly displaced laterally to eject sampled printed sheets and avoid interference with a line of printed sheets conveyed along the conveyance path. Then, the sampling plate retreats to its standby position. The above-described preset pulse umber is determined by converting a preset travel distance of a printed sheet (the length of a printed sheet) into a corresponding number of pluses that are output at a rate corresponding to the printing speed of the rotary press.

According to the apparatus disclosed in Japanese Patent Publication No. 55-31069, an opening portion is provided on one side of the rising section of a conveyance path for conveying printed sheets from the folder unit of a rotary press to a counter stacker or the like. After first sampling member is advanced into a printed sheets line, second sampling member, which is located upstream of and operates independently of the first sampling member, is plunged into the printed sheets line to thereby sample a small number of printed sheets through the opening portion. Upon completion of the sampling, the first and second sampling members retreat in a manner to avoid interference with the printed sheets line.

A contactor for operating a limit switch for detecting the leading end of first printed sheet subsequent to printed sheets to be sampled is projected at a predetermined position of the conveyance path located downstream of a predetermined plunge position of the second sampling member, whereby it is readied to detect the leading end of the subsequent printed sheet. A preset distance is defined as a distance obtained by subtracting half of an overlap pitch of printed sheets from the distance between the position of the contactor and the predetermined plunge position of the second sampling member. The preset distance is then converted into a corresponding number of pulses that are output at a rate corresponding to the printing speed of a rotary press. As soon as a sampling start button is pressed ON to advance the first sampling member, counting of pulses of the electric pulse signal starts in order to calculate the travel distance of a printed sheet from the counted number of pulses. When the number of counted pulses reaches a number of pulses corresponding to the operating time of the second sampling member, the counting is halted. Then, when a detection signal is issued from the limit switch, the counting resumes for counting the rest of the set number of pulses. Upon completion of counting of the set number of pulses, the second sampling member is instructed to plunge into a printed sheets line.

The apparatus disclosed in Japanese Patent Publication No. 55-5466 includes first sampling member and second sampling member located downstream of the first sampling member. The first sampling member moves between a standby position located away from the printed sheets line and an operation position, where part of a printed sheets line conveyed along the conveyance path extending between the folder unit of a rotary press and a counter stacker or the like is floated from the conveyance path, so that the printed sheets line is branched. The second sampling member moves between a standby position located away from the printed sheets line and an operation position, where the second sampling member interferes with a required number of printed sheets present downstream in the branched line so as to eject the sampled printed sheets to the exterior of the printed sheets line.

When the first sampling member is angularly displaced into the printed sheets line in response to a manually issued sampling instruction, counting of pulses of an electric pulse signal output at a rate corresponding to the printing speed of a rotary press starts for calculating the travel distance of a printed sheet along the conveyance path from the counted number of pulses. When the number of counted pulses reaches a predetermined pulse number, which has been predetermined through correction for following the printing speed of a rotary press, the second sampling member is plunged into the printed sheets line so as to eject printed sheets to be sampled into an ejection section.

The above-described conventional apparatuses for sampling a small number of printed sheets from a printed sheets conveyance line involve the following problems.

In the apparatus disclosed in Japanese Patent Publication No. 55-31070, when a sampling instruction is manually issued for sampling (hereinafter may be referred to as "inspecting" or "inspection" or "to inspect") printed sheets, the sampling plate having the capture portion immediately advances angularly into the printed sheets line. To sample, for example, two printed sheets for inspection, the length of the sampling plate as measured along a conveyance direction is set to double the aforementioned overlap pitch, assuming that the overlap pitch of printed sheets remains unchanged.

However, the overlap pitch of printed sheets varies due to a disturbance of printed sheets discharged from the folder unit or a disturbance of printed sheets during conveyance. In addition, the operation of the sampling plate is not controlled such that the sampling plate advances into a printed sheets line, which is conveyed at a rate corresponding to a printing speed, at an optimum position of the line. In other words, no specific relation is established between printed sheets to be sampled and the position on a printed sheets line where the capture portion of the sampling plate, which immediately operates in response to a sampling instruction, advances. Thus, the position where the capture portion advances into the printed sheets line is unknown. That is, since means for monitoring an overlap pitch of printed sheets along the conveyance path is not provided, the sampling plate may advance into a line of printed sheets conveyed at nonuniform overlap pitches. In such a case, the sampling plate advances into a printed sheets line at a position inadequate for sampling target printed sheets.

Specifically, the sampling plate, which has the capture portion and advances into a printed sheets line in an angularly displacing manner, advances into the line regardless of the position of the leading end of a printed sheet. As a result, the sampling plate may thrust the leading end of the printed sheet away, cause printed sheets to be folded, block the conveyance of printed sheet, or bite printed sheets, resulting in a disturbance of the flow of the printed sheets line. This in turn may cause a paper jam in the conveyance path.

Also, as soon as the sampling plate is angularly displaced, the ejection plate is angularly displaced in a substantially oblique upward direction, thereby defining a space having a V-shaped cross-section with the sampling plate. For example, two printed sheets captured in this space are separated from the printed sheets line, so that the printed sheets stand stationary in a curved shape. Immediately after the capture portion of the sampling plate advances into a printed sheets line, the limit switch operates to generate an electric signal, which initiates the counting of electric pulses. Upon completion of the counting, a signal indicative of the completion of the counting causes the ejection plate to be angularly displaced downward, and causes the sampling plate having the capture portion to be angularly displaced laterally to a position where the sampling plate does not interfere with a printed sheets line.

Then, a force causing sampled printed sheets to be curved is released. As a result, the sampled printed sheets tend to restore themselves to a straight position due to a restoring force, particularly when the number of pages is relatively large. The leading ends of the thus restored sampled printed sheets tend to touch the contact portion between a roller located above the opening portion and a printed sheets line conveyed along the roller, to thus be caught turbulently in the contact portion, i.e. in the conveyance path. In addition, for example, in the case of a newspaper rotary press which prints at least 120,000 copies per hour, since the tail ends of the curved printed sheets are in contact with a conveyor belt or a conveyor roller located under the opening portion, the tail ends are flipped by the conveyor belt or conveyor roller.

This involves a problem that the thus-flipped tail ends advance ahead of the leading ends, causing turbulence in conveyance of the sampled printed sheets.

Further, the sampling plate is angularly displaced; i.e. moves along a circular path, to advance into a printed sheets line. This arrangement involves a problem that the optimum position and depth of advancement of the capture portion with respect to a printed sheets line vary with the overall thickness of printed sheets or the thickness of a printed sheets line, which varies with the number of pages of the printed sheets.

In the apparatus disclosed in Japanese Patent Publication No. 55-31069, as in the one disclosed in Japanese Patent Publication No. 55-31070, when a sampling start button is pressed ON, the first sampling member is angularly displaced along a circular path to advance into a printed sheets line without consideration of disturbance or variation in the printing speed or the overlap pitch of printed sheets. That is, the first sampling member is plunged into the printed sheets line regardless of the positions of printed sheets or the overlap pitches of the printed sheets in the printed sheets line, involving a potential disturbance of the printed sheets line or a potential failure to advance into the printed sheets line at a position adequate for sampling. As a result, as in the apparatus disclosed in Japanese Patent Publication No. 55-31070, the first sampling member may thrust printed sheets away, cause printed sheets to be folded, or bite printed sheets, resulting in a disturbance of the flow of the printed sheets line. This in turn may cause a paper jam in the conveyance path.

Also, for example, when two printed sheets are to be inspected, the contactor for operating the limit switch for detecting the leading end of first printed sheet subsequent to the two printed sheets is projected in preparation for detecting the leading end of the subsequent first printed sheet. The preset distance is defined as a distance obtained by subtracting half of an overlap pitch of printed sheets from the distance between the position of the contactor and the predetermined plunge position of the second sampling member. The preset distance is determined by converting the present distance into a corresponding number of pulses that are output at a rate corresponding to the printing speed of a rotary press. As soon as the sampling start button is pressed ON to advance the first sampling member, counting of pulses of the electric pulse signal starts in order to calculate the travel distance of a printed sheet from the counted number of pulses. When the number of counted pulses reaches a pulse number corresponding to the operating time of the second sampling member, the counting is halted. Then, when a detection signal is issued from the limit switch, the counting resumes for counting the rest of the set number of pulses. Upon completion of counting of the set number of pulses, the second sampling member is instructed to plunge into a printed sheets line so as to eject the printed sheets from the printed sheets line.

That is, when the sampling start button is arbitrarily pressed ON, the first sampling member is immediately operated without consideration of the positions of printed sheets. Thereafter, upon completion of counting of the rest of the set number of pulses after a signal is received from the limit switch for detecting the leading end of a printed sheet, the second sampling member is plunged into a printed sheets line. In other words, the plunging operation of the second sampling member is initiated in accordance with a predetermined operational relation with the leading end of a printed sheet which has caused the limit switch to operate. However, since the overlap pitches of printed sheets in a printed sheets line are not monitored, and the second sampling member is plunged into a printed sheets line without adjustment of its operational relation with printed sheets to be sampled, the second sampling member frequently plunges into a printed sheets line having irregular overlap pitches of printed sheets. In addition, as in the case of the first sampling member, the second sampling member plunges into a printed sheets line at a position inadequate for sampling target printed sheets. As a result, the flow of the printed sheets line is disturbed, or such a plunge damages printed sheets.

Further, the limit switch for detecting the leading end of first printed sheet subsequent to target printed sheets includes a paper guide which also serves as a protector for the contactor of the limit switch. The paper guide is attached indirectly to a shaft for angularly displacing the first sampling member. Accordingly, this arrangement involves a problem that as soon as the first sampling member operates, the paper guide presses a printed sheets line via the first sampling member to interfere with the movement of the printed sheets line, resulting in a disturbance of the flow of the printed sheets line.

The apparatus disclosed in Japanese Patent Publication No. 55-5466 functions in the following manner. When the first sampling member is angularly displaced into the printed sheets line in response to a manually issued sampling instruction, counting of pulses of an electric pulse signal output at a rate corresponding to the printing speed of a rotary press starts for calculating the travel distance of a printed sheet along the conveyance path from the counted number of pulses. When the number of counted pulses reaches a predetermined number of pulses, which has been predetermined through correction for following the printing speed of a rotary press, the second sampling member is plunged into the printed sheets line so as to eject printed sheets to be sampled into an ejection section.

That is, as in the apparatus disclosed in Japanese Patent Publication No. 55-31069, the first and second sampling members are advanced into a printed sheets line without monitoring of overlap pitches of printed sheets in the printed sheets line and without adjustment of their operational relation with printed sheets to be sampled. As a result, the first and second sampling members frequently advance into a printed sheets line having irregular overlap pitches of printed sheets. In addition, the first and second sampling members advance into a printed sheets line at a position inadequate for sampling target printed sheets. Consequently, printed sheets are damaged, the flow of a printed sheets line is disturbed, or the conveyance path is jammed with printed sheets.

SUMMARY OF THE INVENTION

An object of the present invention is to solve the above-mentioned problems in the conventional sampling apparatuses and to provide an apparatus for sampling a small number of printed sheets capable of reliably sampling at any printing speed, for example, two printed sheets for inspection without disturbing the flow of a printed sheets line or damaging printed sheets, which has a simple mechanism, which is controlled in a simple manner to thereby reduce the occurrence of failure, and which enables easy maintenance.

To achieve the above object, the present invention provides an apparatus for sampling a small number of printed sheets, the apparatus being provided in a conveyance path zone and adapted to extract a small number of printed sheets from a conveyance path through an opening portion formed in conveyance means. Two opposed conveyance means constitute the conveyance path zone through which folded printed sheets discharged from a rotary press are conveyed in a line and overlap each other at a certain pitch. The opposed conveyance means hold the printed sheets line from both sides thereof to thereby convey the printed sheets line. The opening portion is formed in the conveyance means which holds the printed sheets line on the side where leading ends of printed sheets are not exposed.

The apparatus of the present invention includes a linearly movable frame, a sampling plate, a sampling-plate driving means, linearly-movable-frame driving means, leading-end detection means, side detection means, pulse signal output means, and a sampling control means. The linearly movable frame is provided such that it can advance into and retreat from the printed sheets line substantially perpendicularly to the printed sheets line in a portion of the conveyance path zone corresponding to the opening portion. The sampling plate is provided on the linearly movable frame in the following manner: when the linearly movable frame advances, the sampling plate traverses the portion of the conveyance path zone corresponding to the opening portion and reaches the opening portion, maintaining first posture in which the sampling plate is substantially parallel to the printed sheets line in the portion of the conveyance path zone; and when the linearly movable frame retreats, the sampling plate changes its posture to second posture in which the sampling plate is substantially perpendicular to the printed sheets line and situated outside a side edge of the printed sheets line in order to avoid interference with the printed sheets line during its retreat. The sampling plate has a capture portion which contacts the leading ends of a predetermined number of printed sheets and blocks their conveyance when the sampling plate traverses the portion of the conveyance path zone. The sampling plate has a length determined by the number of printed sheets to be sampled and an overlap pitch of printed sheets in the printed sheets line, as measured along the printed sheets line in the portion of the conveyance path zone corresponding to the opening portion. The sampling-plate driving means selectively displaces the sampling plate to the first or second posture. The linearly-movable-frame driving means advances and retreats the linearly movable frame substantially perpendicularly to the printed sheets line in the portion of the conveyance path zone corresponding to the opening portion, and advances and retreats the sampling plate in a temporarily stoppable manner in the portion of the conveyance path zone corresponding to the opening portion. The leading-end detection means detects the leading end of each printed sheet conveyed by the conveyance means and outputs a corresponding detection signal. The side detection means detects a projection beyond a predetermined position of a side edge of a printed sheet conveyed by the conveyance means and outputs a corresponding detection signal. The pulse signal output means outputs a pulse signal having pulses proportional to the conveyance distance of a printed sheet conveyed by the conveyance means. The sampling control means is connected to the leading-end detection means and the pulse signal output means, and, as needed, to the side detection means. After confirming that printed sheets are properly conveyed by the conveyance means i.e. at a proper overlap pitch of printed sheets and with the side edges of printed sheets being situated properly, based on output signals received from the leading-end detection means, the side detection means, and the pulse signal output means, the sampling control means operates the sampling-plate driving means and the linearly-movable-frame driving means in a predetermined sequence to thereby sample printed sheets through use of the sampling plate.

Printed-sheets braking means may be provided at a lower position of the opening portion in order to receive the tail end portions of printed sheets when the printed sheets are captured at their leading ends by the capture portion of the sampling plate and taken out through the opening portion. The linearly movable frame may have advancement-depth-into-printed-sheets-line adjustment means for adjusting the temporarily stopping position of the sampling plate in the moving direction of the sampling plate in the portion of the conveyance path zone corresponding to the opening portion.

Further, a predetermined-number-of-printed-sheets counter may be provided. The predetermined-number-of-printed-sheets counter causes the sampling control means to start the sampling-plate driving means and the linearly-movable-frame driving means for each conveyance of a predetermined number of printed sheets.

The apparatus for sampling a small number of printed sheets according to the present invention achieves the following effects.

(1) In response to a sampling start instruction issued at arbitrary timing, the side detection means functions to check a printed sheets line for a sideward disturbance of printed sheets, and the leading-end detection means and the pulse signal output means cooperatively check the printed sheets line for overlap pitches of printed sheets, followed by operating time correction, which will be described later. Thus, even when the printed sheets line involves a sideward disturbance of printed sheets or irregular overlap pitches of printed sheets, any number of printed sheets, for example, two printed sheets can be reliably sampled from a predetermined number of printed sheets whose overlap pitches fall within a predetermined allowable range.

(2) The sampling control means processes detection signals received from the leading-end detection means and the side detection means, both located downstream of a sampling position. Based on a pulse signal output from the pulse signal output means, the sampling control means counts the number of pulses obtained by subtracting the number of pulses equivalent to the operating time of the sampling plate for advancement to the sampling position (the number of pulses corrected for operating time) from the number of pulses equivalent to the conveyance of a target printed sheet to a predetermined position located before the sampling position. Upon completion of this counting, a counting completion signal is issued to operate the sampling plate. Thus, the capture portion can reliably advance to the sampling position and capture target printed sheets without being affected by a printing speed.

(3) In contrast with a conventional apparatus in which a plurality of sampling members are angularly displaced to plunge into a printed sheets line, the sampling plate moves linearly in a perpendicular relation with the printed sheets line, and the sampling control means controls the timing of advancement of the sampling plate having the integrally formed capture portion into the printed sheets line. Thus, the positional relation between the advancement of the sampling plate and the printed sheets line is always sustained constant, thereby avoiding a disturbance of the flow of the printed sheets line and a potential damage to printed sheets.

(4) As described above, the sampling plate, together with the linearly movable frame, moves linearly except that it is angularly displaced to avoid interference with both edges of the printed sheets line when it is retreated to its standby position. Thus, the apparatus has a very simple structure, features less frequency of failure, provides high safety for workers, and is inexpensive.

(5) When the printed-sheets braking means is provided, printed sheets captured by the sampling plate and curved due to the blocking of their conveyance are supported at their tail ends by the printed-sheets braking means and secured at their leading ends by the capture portion. The thus-captured printed sheets are transferred onto a conveyor belt by the linearly moving sampling plate. Thus, the ejection of the captured printed sheets is smoothly performed. Accordingly, in contrast with a conventional apparatus in which a sampling member is angularly displaced to plunge into a printed sheets line with a resultant strong impact on sampled printed sheets, the apparatus according to the present invention is free from a disturbance of the flow of the printed sheets line and a damage to printed sheets due to such an impacting ejection of sampled printed sheets.

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which.

DESCRIPTION OF THE PREFERRED EMBODIMENT

An embodiment of the present invention will now be described with reference to the drawings.

Figure 1:
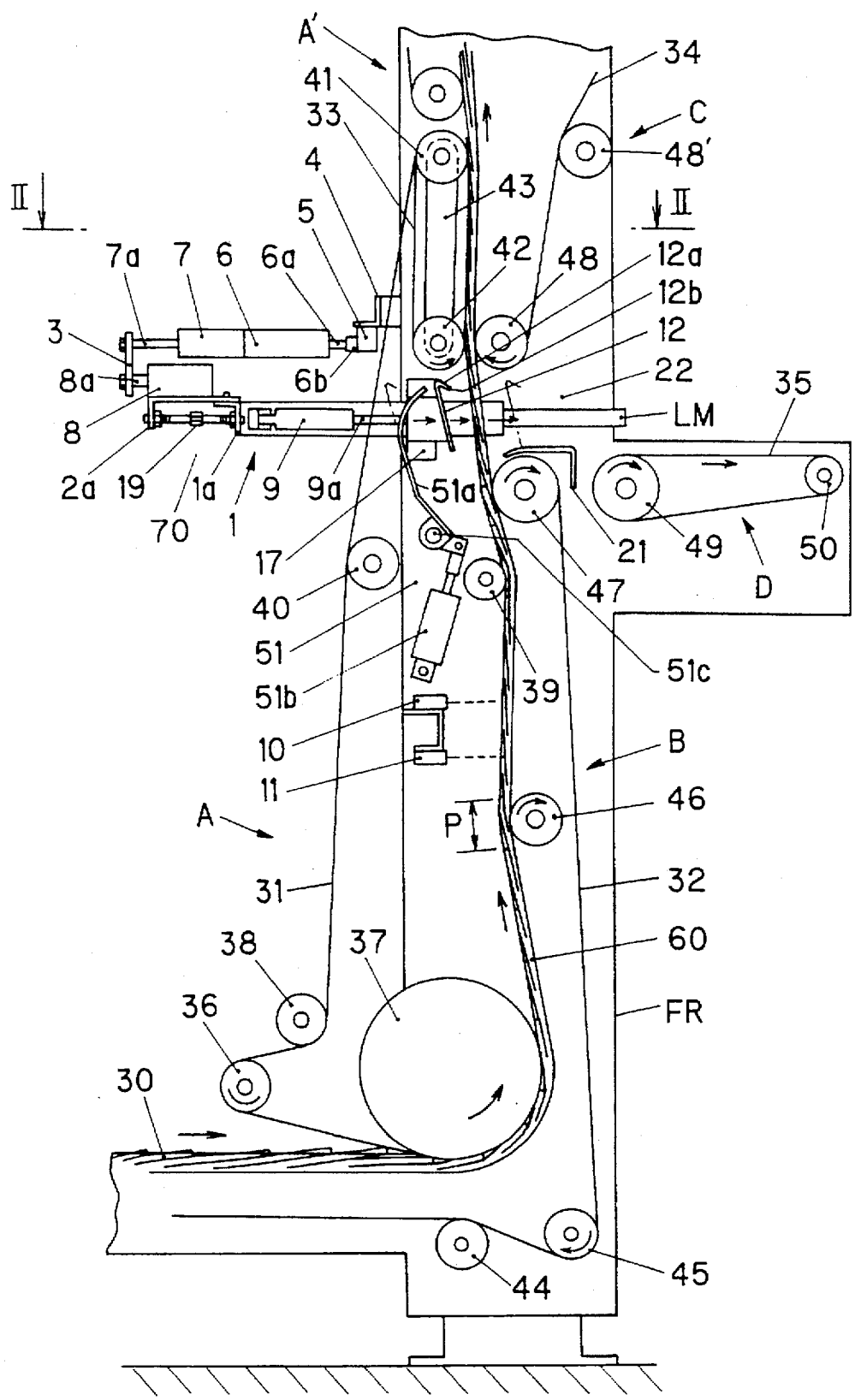
FIG. 1 is a side view of a printed sheets conveying equipment having an apparatus for sampling a small number of printed sheets according to an embodiment of the present invention.

An apparatus for sampling a small number of printed sheets according to the embodiment of the present invention shown in FIG. 1 is provided in a conveyance path composed of belt conveyors for conveying a printed sheets line 30 to a counter stacker or a like subsequent apparatus. In the printed sheets line 30, folded printed sheets discharged from a rotary press overlap each other at appropriate predetermined pitches. As shown in FIG. 1, the conveyance path includes a horizontal section extending from the left to the right, an upright section, an inclined section which slightly inclines leftward, and another upright section in this order.

As shown in FIG. 1, in a belt conveyor A, which is part of the conveyance path, a conveyor belt 31 is looped around and mounted on a driving roller 37, a follower roller 39, a swing roller 42, and follower rollers 41, 40, 38, and 36 and is displaced counterclockwise. The belt conveyor 31 defines the upright section of the conveyance path between the driving roller 37 and the follower roller 39, the inclined section between the follower roller 39 and the swing roller 42, and another upright section between the swing roller 42 and the follower roller 41. The belt conveyor A is followed by a belt conveyor A' which is located above the belt conveyor A and constitutes a further upright section of the conveyance path.

The swing roller 42 is rotatably mounted on the lower end of a swing arm 43, which is angularly displaceably supported at its upper end by the support shaft of the top follower roller 41 of the belt conveyor A and extends downward. Further, the swing roller 42 is opposed to a bottom follower roller 48 of a belt conveyor C, which will be described later, while an appropriate spacing is sustained therebetween. The swing roller 42 is appropriately pressed by an unillustrated pressing means toward the follower roller 48. A conveyor belt 33 is looped around and mounted on the swing roller 42 and the follower roller 41 and is displaced counterclockwise.

In a belt conveyor B opposed to the belt conveyor A in the upright and inclined sections, a conveyor belt 32 is looped around and mounted on a top driving roller 47, follower rollers 45 and 44, an unillustrated follower roller located on the side of the folder unit of a rotary press (leftward in FIG. 1), the driving roller 37, and a follower roller 46 and is displaced clockwise in FIG. 1. The conveyor belt 32 defines the horizontal section of the conveyance path between the unillustrated follower roller located on the side of the folder unit of a rotary press and the driving roller 37 and the upright and inclined sections between the driving roller 37 and the driving roller 47.

At the boundary between the horizontal section and the subsequent upright section of the belt conveyor B, the conveyor belt 32 is looped around on the driving roller 37 via the conveyor belt 31 and the printed sheets line 30. In the section between the follower roller 46 and the driving roller 47, the conveyor belt 32 contacts the follower roller 39 of the belt conveyor A via the conveyor belt 31 and the printed sheets line 30, thereby defining an inclined section between the follower roller 39 and the driving roller 47.

A belt conveyor C is provided above the belt conveyor B such that spacing is formed therebetween so as to form an opening portion 22 for sampling printed sheets therethrough, which will be described later, and that the belt conveyor C is opposed to the belt conveyors A and A' in the upright section. In the belt conveyor C, a conveyor belt 34 is looped around and mounted on the bottom follower roller 48 opposed to the swing roller 42 of the belt conveyor A, a follower roller 48', and an unillustrated driving roller, thereby defining the upright section, and is displaced clockwise.

The distance between the axis of the top driving roller 47 of the belt conveyor B and that of the bottom follower roller 48 of the belt conveyor C is set shorter than the length of a conveyed printed sheet as measured in the direction of conveyance and longer than a length obtained by subtracting a predetermined overlap pitch P from the printed sheet length, thereby preventing printed sheets of the printed sheets line 30 from slipping down or falling down through the opening portion 22.

A belt conveyor D is horizontally provided on the right-hand side of the opening portion 22 in FIG. 1 in order to convey sampled printed sheets or printed sheets discharged as waste. Specifically, an upstream driving roller 49 of the belt conveyor D is provided horizontally opposingly to the top driving roller 47 of the belt conveyor B such that an appropriate spacing is formed therebetween. A conveyor belt 35 is looped around and mounted on the driving roller 49 and a downstream follower roller 50 and is displaced clockwise in FIG. 1 at one-half or a fraction of the running speed of the conveyor belt 32 of the belt conveyor B.

Figure 2:
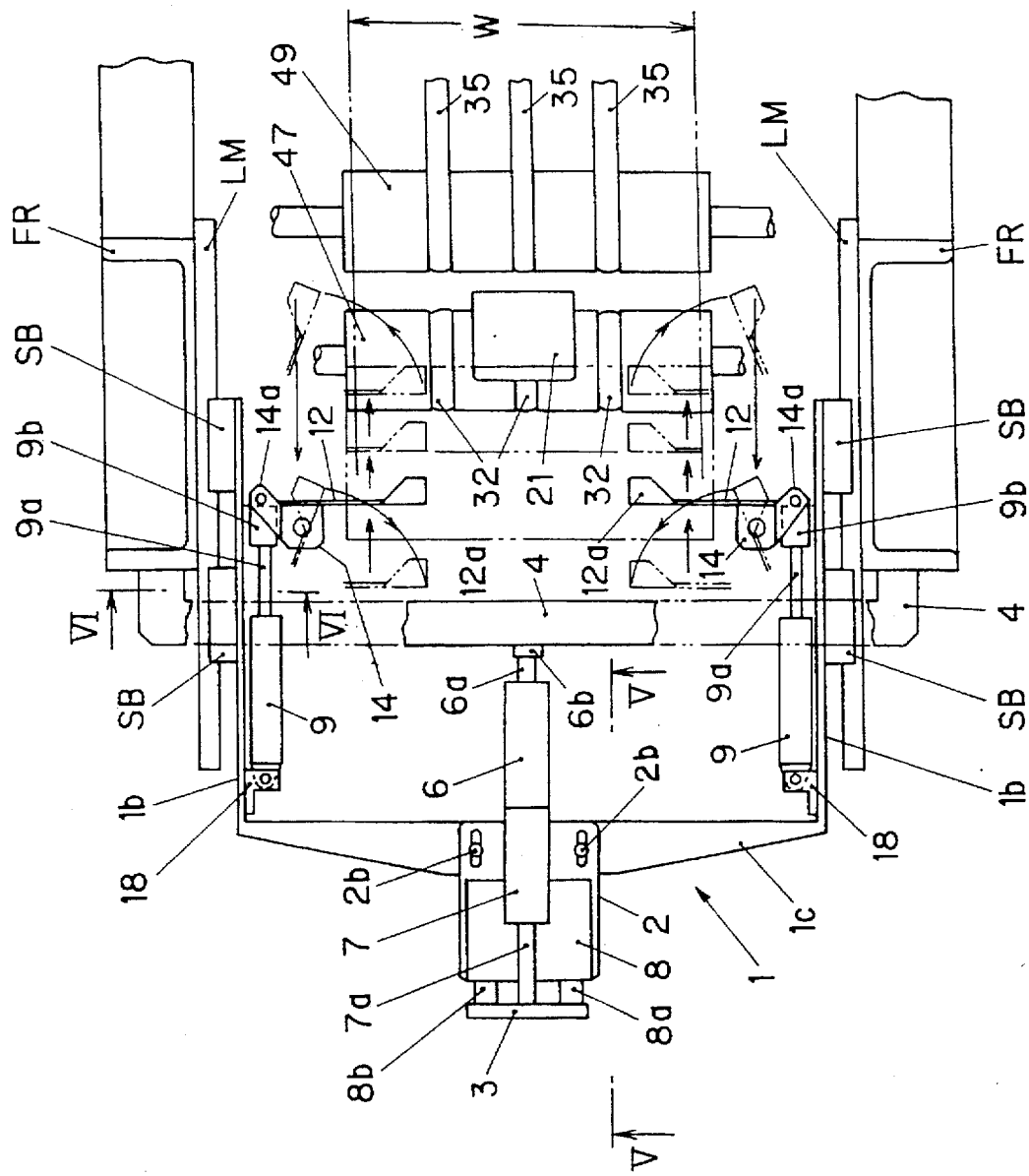
FIG. 2 is a sectional partial view taken along line II—II of FIG. 1.

As shown in FIG. 2, the conveyor belts 32 and 35 each include a plurality of (three in this case) belts arranged in parallel with each other and spaced appropriately. Likewise, the conveyor belts of other belt conveyors described above assume the same arrangement.

The apparatus for sampling a small number of printed sheets will now be described with reference to FIGS. 1, 2, 4, 5, and 6. Most components of the apparatus are located on the left-hand side of the opening portion 22 in FIGS. 1 and 2.

Linear movement guide members LM extending in the right-and-left direction in FIG. 2 are mounted on the opposing side surfaces of two opposed frames FR of the conveyance equipment (disposed on the front and back sides in FIG. 1). A linearly movable frame 1, which includes a connection portion 1c and two leg portions 1b and has the shape of a squarish letter C, is mounted on the linear movement guide members LM via slide blocks SB such that the linearly movable frame 1 can be advanced and retracted in the right-and-left direction in FIGS. 1 and 2, i.e. substantially perpendicularly to the printed sheets line 30 in the opening portion 22. That is, the leg portions 1b are mounted on the slide blocks SB, which, in turn, are slidably mounted on the linear movement guide members LM such that an appropriately space is formed therebetween.

Figure 5:
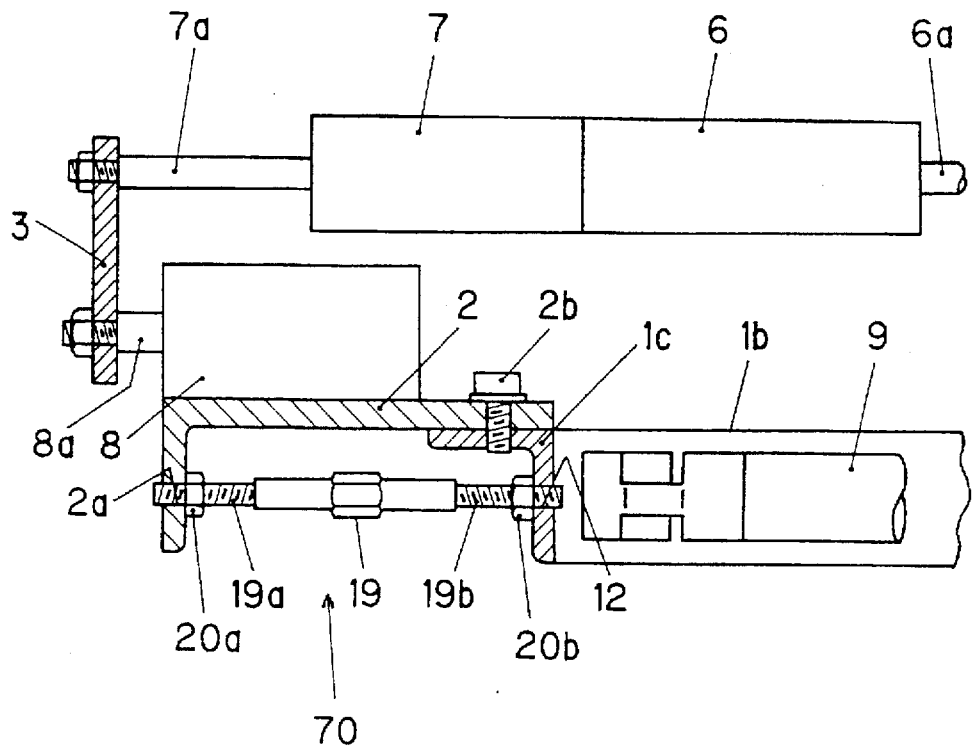
FIG. 5 is a sectional view taken along line V—V of FIG. 2, showing advancement-depth adjustment means for the sampling plate of the apparatus according to the embodiment.

A plate 2 is mounted on the connection portion 1c of the linearly movable frame 1 at the central position such that its position is adjustable in the right-and-left direction in FIG. 2. As shown in FIGS. 2 and 5, two mounting bolts 2b are inserted into elongated holes formed in the plate 2 at both sides and screwed into the connection portion 1c. The connection portion 1c and the plate 2 are connected by an adjustment screw 19 whose both end portions are mutually inversely threaded (one end portion 19a has a left-handed screw, and the other end portion 19b has a right-handed screw, or vice versa) and whose central portion is in the form of a hexagonal bar. The end portion 19a is screwed into a threaded hole 2a formed in the plate 2, whereas the end portion 19b is screwed into a threaded hole 1a formed in the connection portion 1c. Further, lock nuts 20a and 20b are engaged with the end portions 19a and 19b, respectively, against loosening.

The above-described position adjustment means for the plate 2 serves as an advancement-depth-into-printed-sheets-line adjustment means 70 for a sampling plate 12, which will be described later.

As shown in FIGS. 2 and 5, a fluid-pressure cylinder 8 for sampling use is mounted on the plate 2 in the right-and-left direction in FIGS. 2 and 5. A piston rod 8a projects leftward in FIG. 5 from the fluid-pressure cylinder 8. A rigid guide rod 8b is slidably guided by the fluid-pressure cylinder 8 in parallel with the piston rod 8a. The projecting ends of the piston rod 8a and the guide rod 8b are connected by a connection member 3.

A stay 4 is disposed between the opposed two frames FR. A bracket 5 attached to the central portion of the stay 4 is connected to the central portion of the connection member 3 through two axially connected fluid-pressure cylinders 6 and 7 such that piston rods 6a and 7a projecting in opposite directions from the cylinders 6 and 7, respectively, are connected to the stay 4 and the connection member 3, respectively. The fluid-pressure cylinder 6 is for preparation use. The projecting end of the piston rod 6a of the fluid-pressure cylinder 6 is angularly displaceably pin-connected to the bracket 5 via a knuckle 6b. The fluid-pressure cylinder 7 is for ejection use. The projecting end of the piston rod 7a of the fluid-pressure cylinder 7 is connected to the central portion of the connection member 3.

The above-described fluid-pressure cylinder 6 for preparation use, fluid-pressure cylinder 7 for ejection use, and fluid-pressure cylinder 8 for sampling use constitute linearly-movable-frame driving means.

Figure 4:
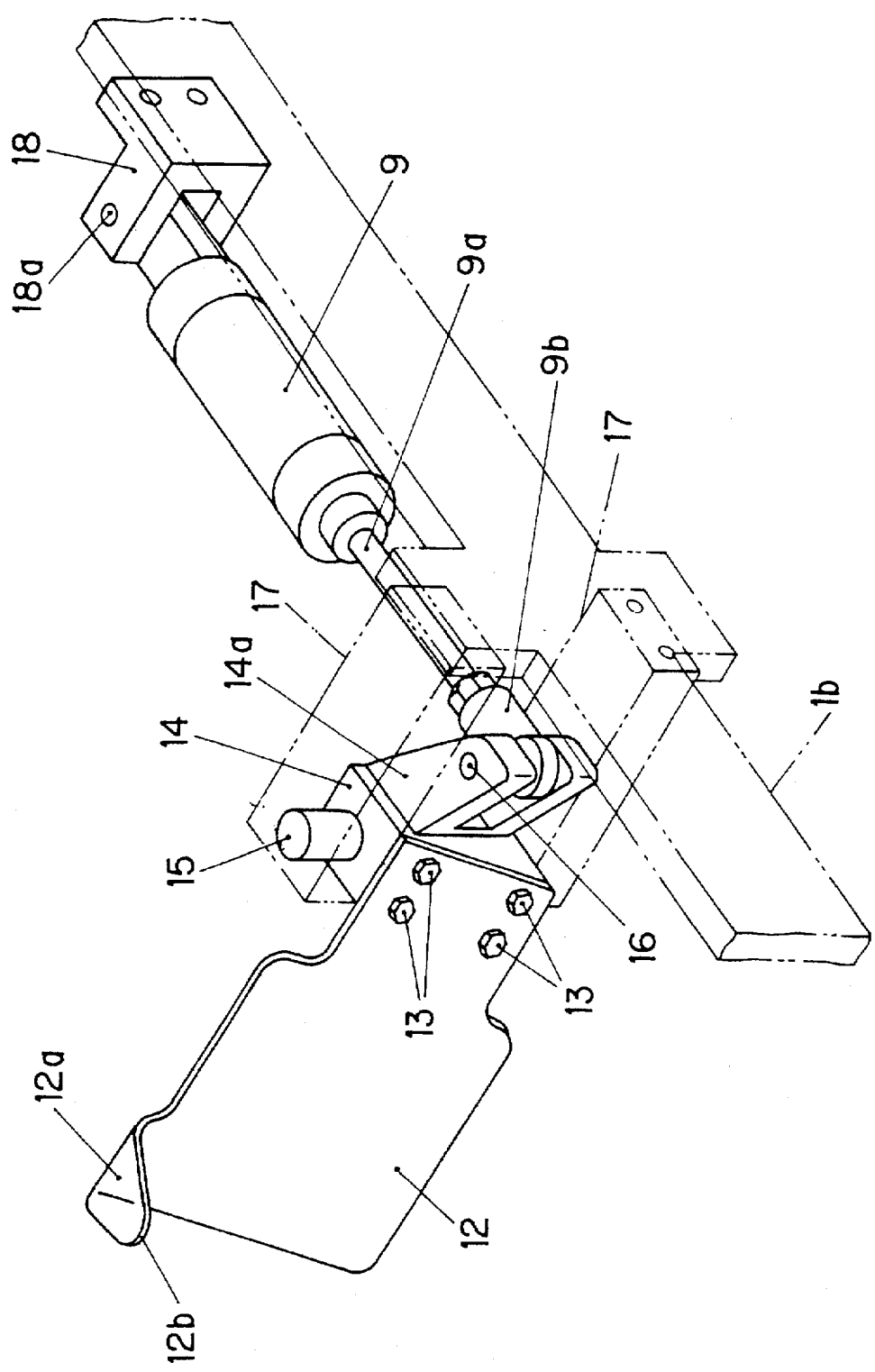
FIG. 4 is a perspective view of an angular displacement mechanism for a sampling plate of the apparatus according to the embodiment.
Figure 6:
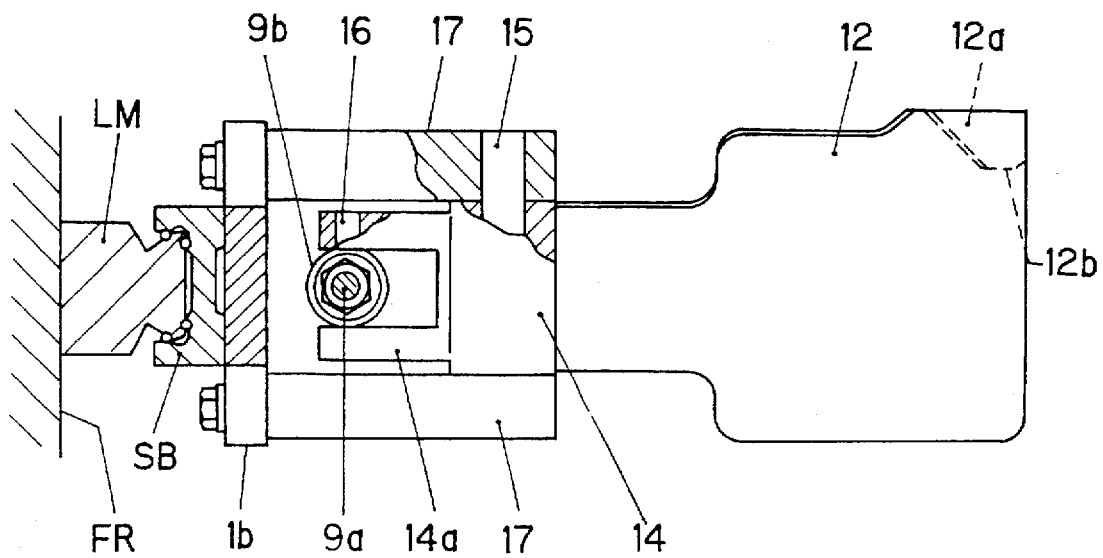
FIG. 6 is a sectional view taken along line VI—VI of FIG. 2, showing the angular displacement mechanism for the sampling place of the apparatus according to the embodiment and a linear movement guide mechanism for the apparatus.

As shown in FIGS. 2, 4, and 6, the two sampling plates 12 are mounted on the corresponding leg portions 1b of the linearly movable frame 1 angularly displaceably about corresponding vertical axes and opposingly to each other. Specifically, the base portion of the sampling plate 12 is removably mounted with bolts 13 on a block 14, into which a shaft 15 is fixedly inserted. The shaft 15 is rotatably bearing-supported at both upper and lower ends thereof by upper and lower brackets 17 mounted on each leg portion 1b.

A fluid-pressure cylinder 9 for angular displacement use, which serve as sampling-plate driving means for angularly displacing the sampling plate 12, is angularly displaceably mounted at its base portion on a bracket 18 via a pin 18a, which bracket 18, in turn, is mounted on the leg portion 1b. The tip end of a piston rod 9a of the fluid-pressure cylinder 9 is angularly displaceably connected to an arm 14a projecting from the block 14, by means of a pin 16 via a knuckle 9b.

In FIGS. 4 and 6, as the piston rod 9a is extended from or retracted into the fluid-pressure cylinder 9, the block 14, i.e. the sampling plate 12 is angularly displaced about the shaft 15. A capture portion 12a is projected from the upper edge of the tip end portion of the sampling plate 12 such that the capture portion 12a extends at an inclination angle of approximately 45 degrees in order to capture printed sheets 30b and 30c in the printed sheets line 30 for sampling (see FIG. 8). The capture portion 12a.

In order to prevent tail ends of sampled printed sheets (see FIG. 7C) from being excessively flipped outward (rightward in FIG. 7C) by the rotating rollers 47, printed-sheets braking means 21 is provided above the roller 47 substantially at the widthwise center of the roller 47. The printed-sheets braking means 21 is a plate having a substantially L-shaped section and an appropriate width. The printed-sheets braking means 21 extends substantially horizontally above the roller 47 toward the opening portion 22 (leftward in FIG. 1) and its end portion opposed to the opening portion 22 is bent downward between the roller 47 and the roller 49 to cover the roller 47.

Figure 3:
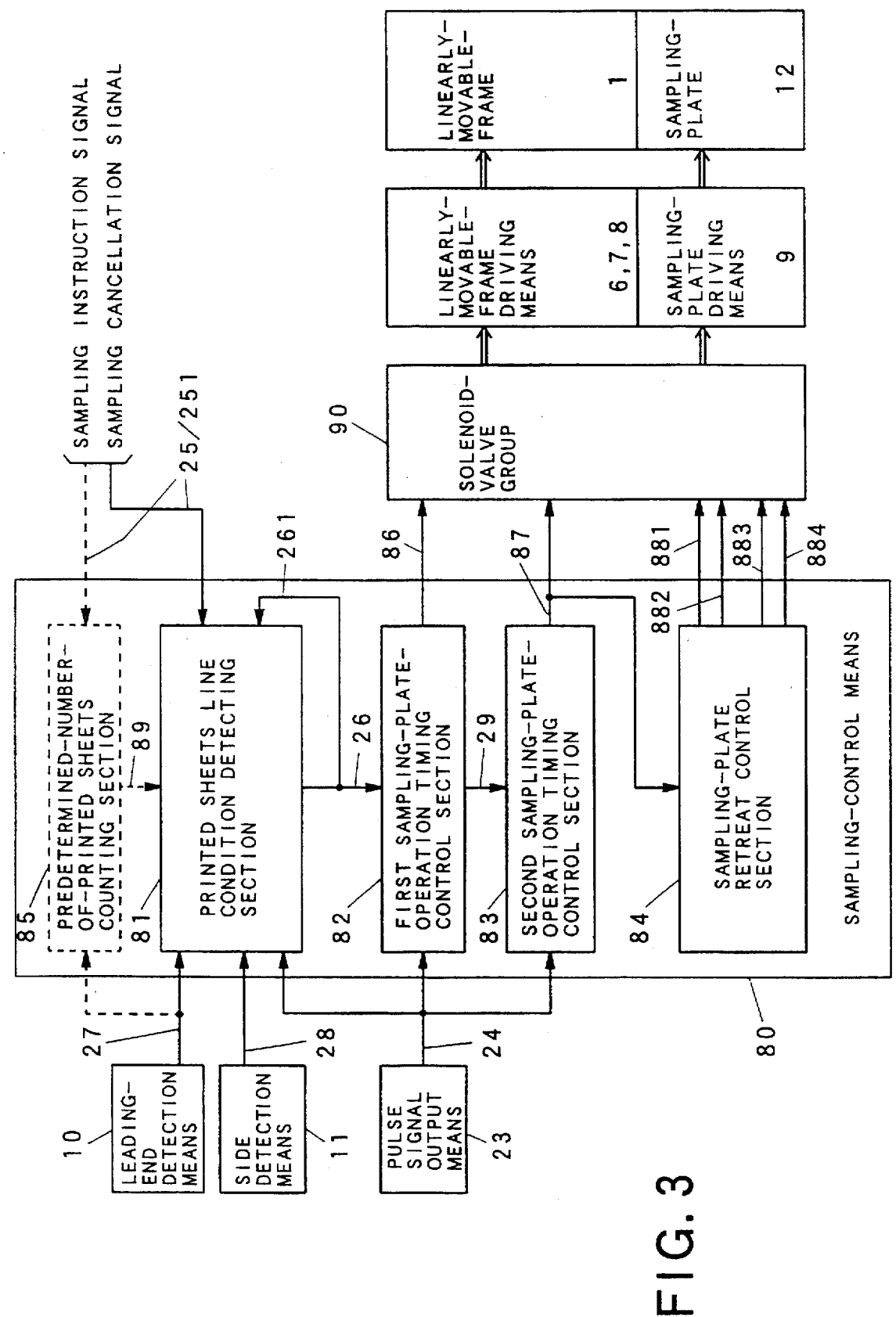
FIG. 3 is a block diagram of the control system of the apparatus according to the embodiment.

As shown in FIGS. 1 and 3, in order to reliably sample printed sheets from a conveyance path 60, under the opening portion 22 is provided leading-end detection means 10 for detecting the leading end of a printed sheet conveyed along the conveyance path 60 and for outputting a detection signal 27. In the vicinity of the leading-end detection means 10 are provided two side detection means 11 for detecting a projection of a conveyed printed sheet beyond the side edges of the printed sheets line 30.

Preferably, the detection positions of the side detection means 11 are located upstream of the detection position of the leading-end detection means 10 in the conveyance direction of printed sheets and within a distance shorter than the length of a printed sheet as measured in the conveyance direction. There is further provided a pulse signal output means 23 for outputting a pulse signal 24 proportional to the conveyance distance of printed sheets conveyed by the conveyor belts 31, 32, 33, 34, which serve as conveyance means and constitute the conveyance path 60.

Specific examples of the leading-end detection means 10 and the side detection means 11 are photoelectric sensors provided opposingly to the conveyance path 60. A specific example of the pulse signal output means 23 is a rotary encoder operatively coupled with the driving roller 37 or 47.

A pulse signal output means used in a rotary pulse may also be used as the pulse signal output means 23. The side detection means 11 may be omitted when there is no potential occurrence of a projection of a printed sheet beyond the side edges of the printed sheets line 30 or when such a projection of a printed sheet is to such a degree as not to affect the sampling of printed sheets.

As shown in FIG. 3, sampling control means 80 includes a printed sheets line condition detector detecting section 8 for detecting the condition of the printed sheets line 30, first sampling-plate-operation timing control section 82 for controlling the timing of advancing the sampling plates 12 into the conveyance path 60 along which the printed sheets line 30 is conveyed, second sampling-plate-operation timing control section 83 for controlling the timing of thrusting the sampling plates 12 through the conveyance path 60 into the opening portion 22 upon completion of capturing target printed sheets by the capture portions of the sampling plates 12, and a sampling-plate retreat control section 84 for controlling the return operation of the sampling plates 12 from the opening portion 22 to their original positions in an eluding relation with the conveyance path 60.

The above-described component devices of the sampling control means 80 are interconnected to each other so as to exchange signals in control operation, which will be described later, are connected to the external leading-end detection means 10, side detection means 11, and pulse signal output means 23 so as to receive signals therefrom, and are connected to a solenoid-valve group 90 for operating the sampling plates 12 so as to output signals thereto.

The solenoid-valve group 90 for operating the sampling plates 12 are provided in a fluid-pressure circuit, which interconnects a fluid-pressure source (not shown), the linearly-movable-frame driving means, i.e. the fluid-pressure cylinder 6 for preparation use, the fluid-pressure cylinder 7 for ejection use, and the fluid-pressure cylinder 8 for sampling use, and the sampling-plate driving means for angularly displacing the sampling plates 12, i.e. the fluid-pressure cylinder 9 for angular displacement use. As will be described later, the solenoid-valve group 90 selectively operate the fluid-pressure cylinders under control of the sampling control means 80.

When printed sheets are to be sampled periodically and automatically every conveyance of a predetermined number of printed sheets, the sampling control means 80 is provided with a predetermined-number-of-printed-sheets counting section 85, which outputs a signal every completion of counting a predetermined number of printed sheets so as to sequentially perform sampling control by means of the printed sheets line condition detecting section 81 through the sampling-plate retreat control section 84. Instead of using the predetermined-number-of-printed-sheets counting section 85, a downstream counter stacker may be provided with a counter feature similar to the predetermined-number-of-printed-sheets counting section 85 so as to sequentially perform sampling control by means of the printed sheets line condition detecting section 81 through the sampling-plate retreat control section 84 in response to a signal issued by the counter feature.

In the embodiment shown in FIG. 1, a waste ejection device 51 is provided in the vicinity of the opening portion 22. In the waste ejection device 51, a fluid-pressure cylinder 51b for waste ejection use causes a waste ejection fork 51a to be angularly displaced about a shaft 51c. Since the waste ejection device 51 is not directly related to the present invention, no further description thereof is omitted.

The operation and action of the above-described apparatus for sampling a small number of printed sheets will now be described. The description below handles a single sampling plate 12, as needed, for simplification of the description.

Figure 8A:
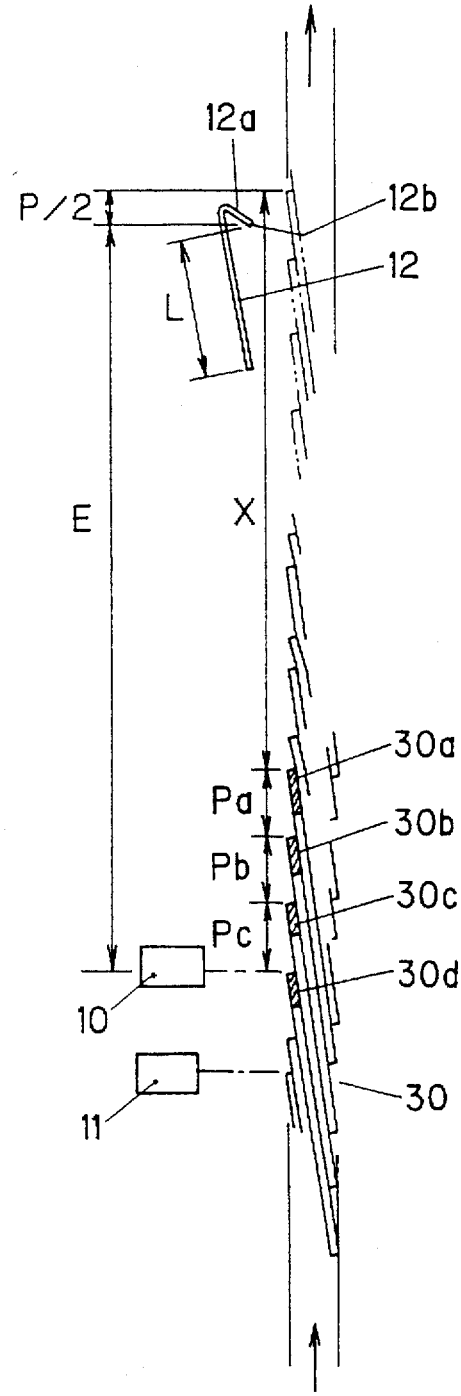
FIGS. 8A and 8B are views showing the timing of advancement into a printed sheets line of the sampling plate of the apparatus according to the embodiment.

First, the relation between the sampling plate 12 and the printed sheets line 30 will be described with reference to FIGS. 8A and 8B. In FIG. 8A, assuming that two printed sheets are to be sampled, and an overlap pitch of printed sheets in the printed sheets line 30 is taken as P (see FIG. 1), the length L of the sampling plate 12 is set substantially to 2P. The length L of the sampling plate 12 is set substantially to the product of the overlap pitch P and the number of printed sheets to be sampled.

Accordingly, the sampling plate 12 having a selected length is selected from among the sampling plates 12 having various lengths. The selected sampling plate 12 is mounted on the block 14 with the bolts 13. The sampling plate 12 is caused to stand by at a standby position located an appropriate distance away from the surface of the printed sheets line 30 not facing the opening portion 22. At this time, the piston rod 7a of the cylinder 7 and the piston rods 9a of the cylinders 9 are in an extended state, whereas the piston rods of other fluid-pressure cylinders are in a retracted state.

When the fluid-pressure cylinder 8 for sampling use operates to advance the sampling plate 12 to the position shown in FIG. 8B as will be described later, the sampling plate 12 having the capture portion 12a formed at its upper edge advances into the printed sheets line 30 by an appropriate depth. Since the optimum advancement depth into the printed sheets line 30 depends on the number of pages of a sheaf of printed sheets or the paper quality of printed sheets, the position of the sampling plate 12 is adjusted in advance by the advancement-depth-into-printed-sheets-line adjustment means 70. Specifically, the mounting bolts 2b and the lock nuts 20a are loosened, and then the adjustment screw 19 is rotated at its central portion by an appropriate tool so as to slide the plate 2 advancingly or retreatively with respect to the connection portion 1c to thereby optimize the position of the sampling plate 12. Subsequently, the mounting bolts 2b and the lock nuts 20a are tightened to fix the sampling plate 12 at the optimum position.

As the rotary press operates, folded printed sheets 30a, 30b, 30c, etc. are discharged from the rotary press and overlap each other, thus forming the printed sheets line 30. The printed sheets line 30 is conveyed by the belt conveyor A, the belt conveyor A', the belt conveyor B, and the belt conveyor C.

In the present embodiment, the apparatus for sampling a small number of printed sheets becomes ready to operate when the main power to the rotary press is turned on.

That is, when the main power is turned on, the leading-end detection means 10 and the side detection means 11 become ready for detection, and the pulse signal output means 23 becomes ready to output a pulse signal.

In this operation-enabled state, an electric instruction signal (hereinafter referred to as a sampling instruction signal 25) for manually or automatically sampling printed sheets is output. Then, in FIG. 8A, the leading-end detection means 10 detects the leading end of each of the printed sheets 30a, 30b, etc. conveyed upward by the belt conveyors A and B. The detection position of the leading-end detection means 10 is located distance E below the tip end 12b of the capture portion 12a of the sampling plate 12, i.e. at a certain upstream position of the printed sheets line 30. The detection signal 27 from the leading-en detection means 10 and the pulse signal 24 from the pulse signal output means 23 are input to the printed sheets line condition detecting section 81, which then calculates an overlap pitch of printed sheets based on the input signals.

For example, when a set overlap pitch P (FIG. 8A) is 50 mm with a tolerance of ±5 mm, i.e. when an allowable overlap pitch ranges from 45 mm to 55 mm, the detection signal 27 for the printed sheet 30a serves as a start signal, and the printed sheets line condition detecting section 81 counts the number of pulses of a pulse signal until the detection signal 27 for the next printed sheet 30b is input thereto. The printed sheets line condition detecting section 81 compares the thus-counted number of pulses with a preset number of pulses of the pulse signal output means 23 equivalent to a conveyance distance of 45 mm to 55 mm, thereby judging whether an overlap pitch Pa of the printed sheets 30a and 30b falls in the allowable overlap pitch range.

Upon reception of the detection signal 27 for the printed sheet 30b from the leading-end detection means 10, the printed sheets line condition detecting section 81 resets the previous count and restarts to count the number of pulses of an input pulse signal. In this manner, subsequent overlap pitches of printed sheets are continuously judged for conformity to the allowable overlap pitch range.

The side detection means 11 detects a projection of a conveyed printed sheet beyond the predetermined side positions of the printed sheets line 30 and outputs a detection signal 28. Each time the detection signal 28 is issued, it resets the count of pulses of the pulse signal 24 from the pulse signal output means 23, the pulses being counted in the printed sheets line condition detecting section 81. Accordingly, even when a certain overlap pitch of printed sheets falls in the allowable overlap pitch range, if the printed sheets project laterally from the printed sheets line 3Q, the overlap pitch is judged to be not allowable. That is, it is judged that an anomaly has occurred in the printed sheets line 30.

Accordingly, the leading-end detection means 10 and the side detection means 11 are located such that the distance therebetween is smaller than the length of a printed sheet as measured in the conveyance direction. Thus, a printed sheet detected by the leading-end detection means 10 is identical to that detected by the side detection means 11 or to a printed sheet immediately before or after that detected by the side detection means 11, thereby facilitating control.

When the above-described preferred positional relation between the leading-end detection means 10 and the side detection means 11 cannot be established, a detection signal delay unit (not shown) is provided for delaying an input of the detection signal 27 or 28 to the printed sheets line condition detecting section 81 in accordance with the conveyance distance of a printed sheet, i.e. the pulse signal 24 output from the pulse signal output means 23. Thus, the printed sheets line condition detecting section 81 receives detection signals from the leading-end detection means 10 and the side detection means 11 as if a printed sheet detected by the leading-end detection means 10 were identical to that detected by the side detection means 11 or to a printed sheet immediately before or after that detected by the side detection means 11.

When the printed sheets line condition detecting section 81 detects that continuous overlap pitches Pa, Pb, Pc, etc. fall in the allowable overlap pitch range and that the side edges of the printed sheets line 30 are not disturbed, the printed sheets line condition detecting section 81 outputs a detection result OK signal 26 indicating that the detection result is acceptable. The detection result OK signal 26 causes the first sampling-plate-operation timing control section 82 to operate.

When the first sampling-plate-operation timing control section 82 counts the number of pulses of the pulse signal 24 output from the pulse signal output means 23 and recognizes that the lead printed sheet 30a of a group of the printed sheets 30a, 30b, 30c, etc. has been conveyed distance X (FIG. 8A) by the conveyor belts 31 and 32 and reached to a predetermined position, the first sampling-plate-operation timing control section 82 outputs first operation signal 86 to the solenoid-valve group 90, thereby operating a solenoid valve for the fluid-pressure cylinder 8 for sampling use. Thus, the piston rod 8a of the fluid-pressure cylinder 8 is extended to advance the sampling plate 12 into the printed sheets line 30. The distance X is obtained by subtracting three times the preset overlap pitch P (e.g. 50 mm) of the printed sheets 30 from the aforementioned distance E and then adding one-half of the overlap pitch P.

The above-mentioned predetermined position for the conveyed printed sheet 30a is determined such that when the sampling plate 12 is advanced into the printed sheets line 30, the tip end 12b of the capture portion 12a is situated substantially at the center of the overlap pitch Pa of the printed sheets 30a and 30b. In this case, since the length of the sampling plate 12 as measured in the printed sheets conveyance direction is determined as mentioned above, the tail end of the sampling plate 12 is naturally situated substantially at the center of the overlap pitch Pc of the printed sheets 30c and 30d.

Figure 8B:
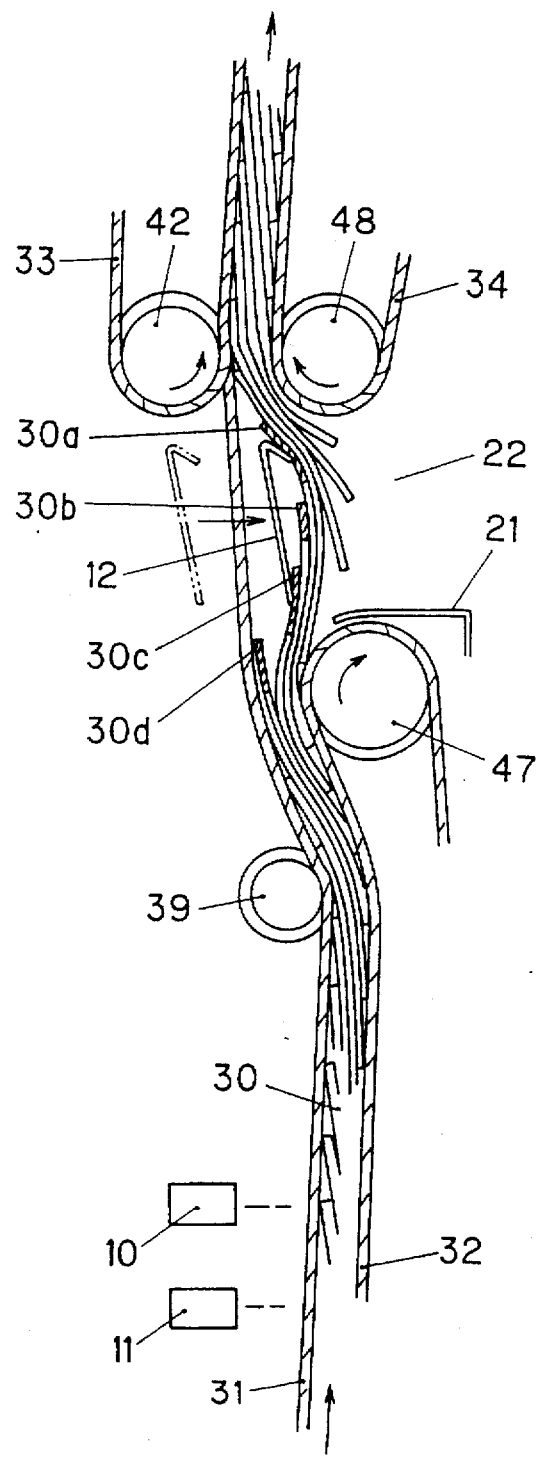

As a result, as shown in FIG. 8B, the capture portion 12a can reliably capture the leading end of the printed sheet 30b, and the tail end of the sampling plate 12 advances substantially into the intermediate position between the leading end of the printed sheet 30c and that of the printed sheet 30d to thereby separate the printed sheet 30c from the printed sheet 30d. Thus, as the printed sheets line 30 moves, the printed sheets 30b and 30c are captured by the capture portion 12a.

The number $N_0$ of pulses counted while a printed sheet is conveyed over a distance equivalent to the preset overlap pitch P and the number N of pulses equivalent to the aforementioned distance X hold the relation, $N = X \cdot N_0/P$. When a sampling-operation time t between the start of operation of the fluid-pressure cylinder 8 and the completion of advancement of the sampling plate 12 into the printed sheets line 30 is negligibly small as compared with a conveyance speed v of the printed sheets line 30, the timing of instructing the fluid-pressure cylinder 8 to operate is when the count of pulses reaches the number N of pulses equivalent to the distance X.

However, as the printing speed of a rotary press increases, the number of printed sheets per unit time increases. Accordingly, the discharge speed of printed sheets must be increased. As a result, the conveyance speed v of the printed sheets line 30 increases accordingly. Thus, the conveyance distance of the printed sheets line 30 during the sampling-operation time t increases. To be consistent with this increase, the timing of issuing an operation instruction for the sampling plate 12, i.e. the timing of outputting the first operation signal 86 must be appropriately adjusted in order to properly advance the tip end 12b of the capture portion 12a to a predetermined position. To this end, the first sampling-plate-operation timing control section 82 is always receiving the pulse signal 24 proportional to the conveyance distance of printed sheets and adjusts the output timing for the first operation signal 86 based on the received pulse signal 24.

That is, upon completion of counting as many pulses as $N-N_t$ (corrected pulse number for sampling operation), i.e. the number N of pulses equivalent to the distance X minus the number $N_t$ of pulses (sampling-operation-time correction pulse number) equivalent to the sampling-operation time t, the first sampling-plate-operation timing control section 82 concurrently outputs the first operation signal 86 to operate the fluid-pressure cylinder 8, thereby reliably advancing the sampling plate 12 with the capture portion 12a connected to the fluid-pressure cylinder 8 into the printed paper line 30 at the position shown in FIG. 8B.

The sampling-operation-time correction pulse number $N_t$ is obtained as follows:

$$N_t = 1000 \cdot (v/60) \cdot (N_0/P) \cdot t$$

where P is an overlap pitch represented in mm, t is a sampling-operation time in sec, and v is a speed in m/min.

As a result of advancement of the sampling plate 12 into the printed sheets line 30, the printed sheets line 30 is halved at the boundary between the printed sheets 30b and 30c to be sampled. The last printed sheet 30a, together with the preceding downstream printed sheets, is conveyed further and captured between the swing roller 42 and the follower roller 48 and is thus conveyed further downstream. During this period, an electric signal 29 generated in response to the operation of the fluid-pressure cylinder 8 or the associated movement of the sampling plate 12 causes the second sampling-plate-operation timing control section 83. Examples of the electric signal 29 include an electric signal issued by a limit switch or proximity switch (not shown).

The thus-activated second sampling-plate-operation timing control section 83 starts to count the number of pulses of the pulse signal 24 output from the pulse signal output means 23 to confirm that the leading end of the printed sheet 30c has been conveyed through the conveyance of the printed sheets line 30 by the conveyor belts 31 and 32 over a sufficient distance to be captured by the capture portion 12a. Upon making this confirmation, the second sampling-plate-operation timing control section 83 outputs second operation signal 87.

Figure 7A:
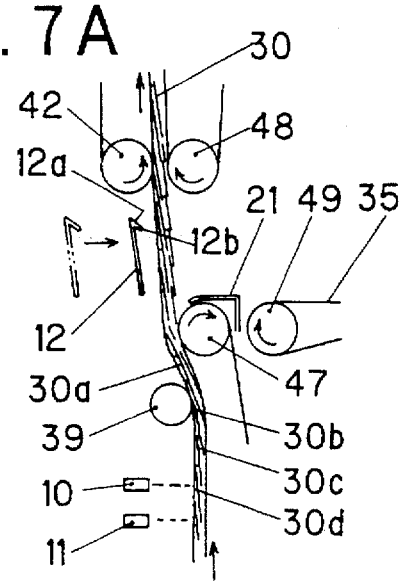
FIGS. 7A to 7G are views showing a sampling operation of the apparatus according to the embodiment.

The second operation signal 87 operates a solenoid valve for the fluid-pressure cylinder 7 for ejection use in the solenoid-valve group 90, thereby retracting the piston rod 7a of the fluid-pressure cylinder 7 and operating the sampling-plate retreat control section 84. As a result of this retraction of the piston rod 7a of the fluid-pressure cylinder 7, the sampling plate 12 standing still in the printed sheets line 30 resumes advancing further while holding the printed sheets 30b and 30c to thereby eject the sampled printed sheets 30b and 30c onto the conveyor belt 35 located outside the printed sheets line 30 (see FIGS. 7B, 7C, and 7D).

Figure 7B:
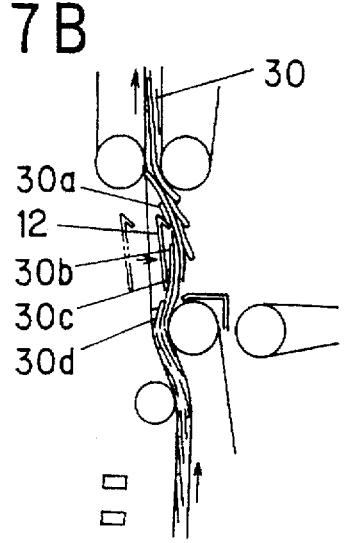
Figure 7C:
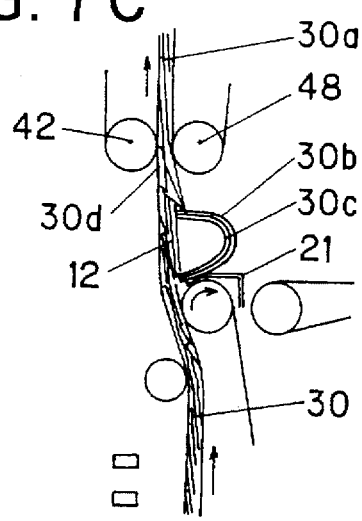
Figure 7D:
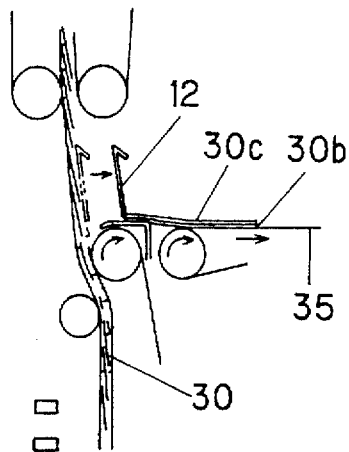

Meanwhile, the upstream lead printed sheet 30d and subsequent printed sheets pass behind the sampling plate 12 along the conveyor belt 31 and are then held between the swing roller 42 and the follower roller 48, thus forming the printed sheets line 30 again in the conveyance path (see FIGS. 7B and 7C).

Figure 7E:
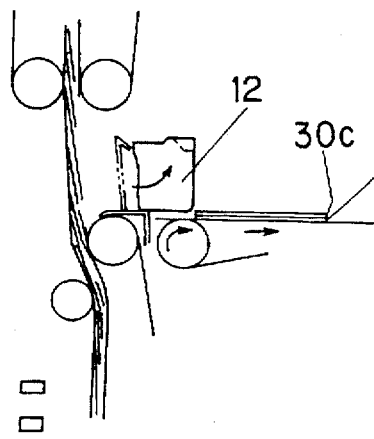

Being operated by the second operation signal 87 output from the second sampling-plate-operation timing control section 83, the sampling-plate retreat control section 84 sequentially outputs signals to the solenoid-valve group 90 to thereby retreat the sampling plate 12 to its standby position. Specifically, these signals are first signal 881 issued to a solenoid valve for the fluid-pressure cylinder 9 for angular displacement use; second signal 882 issued concurrently to a solenoid valve for the fluid-pressure cylinder 6 for preparation use, a solenoid valve for the fluid-pressure cylinder 7 for ejection use, and a solenoid valve for the fluid-pressure cylinder 8 for sampling use; third signal 883 issued to the fluid-pressure cylinder 9, the third signal 883 being another signal issued to the cylinder 9; and fourth signal 884 issued to the fluid-pressure cylinder 6, the fourth signal 884 being another signal issued to the cylinder 6. When the sampling plate 12 moves to the position shown in FIG. 7D and completes its linear advancement, the first signal 881 is issued to operate the fluid-pressure cylinder 9. As a result, the piston rod 9a of the cylinder 9 retracts to thereby angularly displace the sampling plate 12 as shown in FIG. 7E.

Figure 7F:
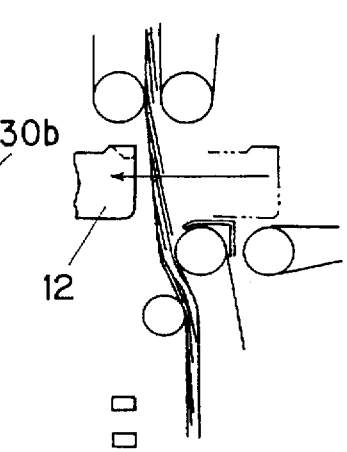
Figure 7G:
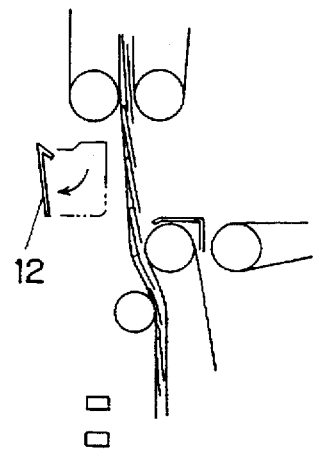

That is, in FIG. 2, the two sampling plates 12 are angularly displaced to positions outside the width W of a printed sheet in the conveyance path, i.e. outside the width W of the printed sheets line 30, thereby avoiding interference with the printed sheets line 30. Next, as a result of output of the second signal 882, the fluid-pressure cylinder 6 for preparation use and the fluid-pressure cylinder 7 for ejection use, and the fluid-pressure cylinder 8 for sampling use operate to thereby extend the piston rods 6a and 7a and retract or contract the piston rod 8a. Accordingly, the sampling plates 12 retreat along the guide members LM to a retracted position behind the printed sheets line 30 shown in FIG. 7F, where the sampling plates 12 do not interfere with the both edges of the printed sheets line 30 when they are angularly displaced back to their original postures. Then, as a result of output of the third signal 883, the fluid-pressure cylinders 9 for angular displacement operate to thereby extend the piston rods 9a. Accordingly, the sampling plates 12 are angularly displaced back to their original postures shown in FIG. 7G.

Further, as a result of output of the fourth signal 884, the fluid-pressure cylinder 6 for preparation use operates to thereby retract the piston rod 6a. Accordingly, the sampling plates 12 return to their standby positions in the vicinity of the conveyance path as shown in FIG. 7A, thus preparing for the next sampling operation.

Thus, one cycle of sampling printed sheets in the embodiment has been completed. If the component features of the sampling control means 80 are all left active, the printed sheets line condition detecting section 81 will keep outputting the detection result OK signal 26. Thus, each time the detection result OK signal 26 is output, a trailing differential signal 261 by differentiating the trailing edge of the signal 26 is issued to thereby turn off the printed sheets line condition detecting section 81, thus preventing the sampling of printed sheets from being repeated.

When sampling printed sheets is to be automatically performed every completion of conveyance of a predetermined number of printed sheets, the predetermined-number-of-printed-sheets counting section 85 or an unillustrated counter stacker is adapted to output a predetermined-number-of-printed-sheets counting completion signal 89 to thereby turn on the printed sheets line condition detecting section 81 in order to start sampling each time a predetermined number of printed sheets are conveyed.

When a stop or emergency stop signal for the rotary press is issued, a sampling cancellation signal 251 is also issued. The sampling cancellation signal 251 resets the printed sheets line condition detecting section 81 and the predetermined-number-of-printed-sheets counting section 85 to initialize them and turns off the printed sheets line condition detecting section 81.

In the present embodiment, various fluid-pressure cylinders are used to advance and retreat the sampling plate 12. However, these fluid-pressure cylinders may be replaced by a single fluid-pressure cylinder having a stopping feature which enables the piston to stop at any position. In this case, operation control may be performed appropriately for this arrangement. Thus, the above-described action and effect can be achieved in a simpler structure. Also, by forming movable members of the fluid-pressure cylinders from light-weight high-rigidity materials, the fluid-pressure cylinders can be further reduced in size.

Obviously, numerous modifications and variations of the present invention are possible in light of the above teachings. It is therefore to be understood that within the scope of the appended claims, the present invention may be practiced otherwise than as specifically described herein.

What is claimed is:

1. An apparatus for sampling a small number of printed sheets, provided in a conveyance path zone and adapted to sample a small number of printed sheets from a conveyance path which is formed by two opposed conveyance means constituting the conveyance path zone and through which folded printed sheets discharged from a rotary press are conveyed in a line and overlap each other at a certain pitch while being held by the opposed conveyance means from both sides thereof, the sampled printed sheets being taken out of the printed sheets line through an opening portion formed in the conveyance means which holds the printed sheets line on the side where leading ends of printed sheets are not exposed, said apparatus comprising:

a linearly movable frame provided such that it can advance into and retreat from the printed sheets line substantially perpendicularly to the printed sheets line in a portion of the conveyance path zone corresponding to said opening portion;

a sampling plate provided on said linearly movable frame, when said linearly movable frame advances, said sampling plate traversing the portion of the conveyance path zone corresponding to said opening portion and reaching said opening portion while maintaining a first posture in which said sampling plate is substantially parallel to the printed sheets line in the portion of the conveyance path zone corresponding to said opening portion, when said linearly movable frame retreats, said sampling plate changing its posture to a second posture in which said sampling plate is substantially perpendicular to the printed sheets line and situated outside a side edge of the printed sheets line in order to avoid interference with the printed sheets line during its retreat, and said sampling plate having a capture portion which contacts the leading ends of a predetermined number of printed sheets and blocks their conveyance when said sampling plate traverses the portion of the conveyance path zone and having a length determined by the number of printed sheets to be sampled and an overlap pitch of printed sheets in the printed sheets line, as measured along the printed sheets line in the portion of the conveyance path zone corresponding to said opening portion;

sampling-plate driving means for selectively displacing said sampling plate to the first or second posture;

linearly-movable-frame driving means for advancing and retreating said linearly movable frame substantially perpendicularly to the printed sheets line in the portion of the conveyance path zone corresponding to said opening portion, and for advancing and retreating said sampling plate in a temporarily stoppable manner in the portion of the conveyance path zone corresponding to said opening portion;

leading-end detection means for detecting the leading end of each printed sheet conveyed by said conveyance means and for outputting a corresponding detection signal;

pulse signal output means for outputting a pulse signal having pulses proportional to the conveyance distance of a printed sheet conveyed by said conveyance means; and sampling control means connected to said leading-end detection means and said pulse signal output means, after confirming that the overlap pitch of printed sheets conveyed by said conveyance means is proper, based on output signals received from said leading-end detection means and said pulse signal output means, said sampling control means operating said sampling-plate driving means and said linearly-movable-frame driving means in a predetermined sequence to thereby sample printed sheets through use of said sampling plate.

2. An apparatus for sampling a small number of printed sheets according to claim 1, further comprising printed-sheets braking means which is provided at a lower position of said opening portion in order to receive the tail end portions of printed sheets when the printed sheets are captured at their leading ends by the capture portion of said sampling plate and taken out through said opening portion.

3. An apparatus for sampling a small number of printed sheets according to claim 2, wherein said linearly movable frame comprises advancement-depth-into-printed-sheets-line adjustment means for adjusting the temporarily stopping position of said sampling plate in the moving direction of said sampling plate in the portion of the conveyance path zone corresponding to said opening portion.

4. An apparatus for sampling a small number of printed sheets according to claim 3, further comprising a predetermined-number-of-printed-sheets counter for causing said sampling control means to start said sampling-plate driving means and said linearly-movable-frame driving means for each conveyance of a predetermined number of printed sheets.

5. An apparatus for sampling a small number of printed sheets according to claim 2, further comprising a predetermined-number-of-printed-sheets counter for causing said sampling control means to start said sampling-plate driving means and said linearly-movable-frame driving means for each conveyance of a predetermined number of printed sheets.

6. An apparatus for sampling a small number of printed sheets according to claim 5, further comprising a predetermined-number-of-printed-sheets counter for causing said sampling control means to start said sampling-plate driving means and said linearly-movable-frame driving means for each conveyance of a predetermined number of printed sheets.

7. An apparatus for sampling a small number of printed sheets according to claim 1, wherein said linearly movable frame comprises advancement-depth-into-printed-sheets-line adjustment means for adjusting the temporarily stopping position of said sampling plate in the moving direction of said sampling plate in the portion of the conveyance path zone corresponding to said opening portion.

8. An apparatus for sampling a small number of printed sheets according to claim 1, further comprising a predetermined-number-of-printed-sheets counter for causing said sampling control means to start said sampling-plate driving means and said linearly-movable-frame driving means for each conveyance of a predetermined number of printed sheets.

9. An apparatus for sampling a small number of printed sheets, provided in a conveyance path zone and adapted to sample a small number of printed sheets from a conveyance path which is formed by two opposed conveyance means constituting the conveyance path zone and through which folded printed sheets discharged from a rotary press are conveyed in a line and overlap each other at a certain pitch while being held by the opposed conveyance means from both sides thereof, the sampled printed sheets being taken out of the printed sheets line through an opening portion formed in the conveyance means which holds the printed sheets line on the side where leading ends of printed sheets are not exposed, said apparatus comprising:

a linearly movable frame provided such that it can advance into and retreat from the printed sheets line substantially perpendicularly to the printed sheets line in a portion of the conveyance path zone corresponding to said opening portion;

a sampling plate provided on said linearly movable frame, when said linearly movable frame advances, said sampling plate traversing the portion of the conveyance path zone corresponding to said opening portion and reaching said opening portion while maintaining a first posture in which said sampling plate is substantially parallel to the printed sheets line in the portion of the conveyance path zone corresponding to said opening portion, when said linearly movable frame retreats, said sampling plate changing its posture to a second posture in which said sampling plate is substantially perpendicular to the printed sheets line and situated outside a side edge of the printed sheets line in order to avoid interference with the printed sheets line during its retreat, and said sampling plate having a capture portion which contacts the leading ends of a predetermined number of printed sheets and blocks their conveyance when said sampling plate traverses the portion of the conveyance path zone and having a length determined by the number of printed sheets to be sampled and an overlap pitch of printed sheets in the printed sheets line, as measured along the printed sheets line in the portion of the conveyance path zone corresponding to said opening portion;

sampling-plate driving means for selectively displacing said sampling plate to the first or second posture;

linearly-movable-frame driving means for advancing and retreating said linearly movable frame substantially perpendicularly to the printed sheets line in the portion of the conveyance path zone corresponding to said opening portion, and for advancing and retreating said sampling plate in a temporarily stoppable manner in the portion of the conveyance path zone corresponding to said opening portion;

leading-end detection means for detecting the leading end of each printed sheet conveyed by said conveyance means and for outputting a corresponding detection signal;

side detection means for detecting a projection beyond a predetermined position of a side edge of a printed sheet conveyed by said conveyance means and for outputting a corresponding detection signal;

pulse signal output means for outputting a pulse signal having pulses proportional to the conveyance distance of a printed sheet conveyed by said conveyance means; and sampling control means connected to said leading-end detection means, said pulse signal output means, and said side detection means, after confirming that the overlap pitch of printed sheets conveyed by said conveyance means is proper and that the side edges of the printed sheets are situated properly, based on output signals received from said leading-end detection means, said side detection means, and said pulse signal output means, said sampling control means operating said sampling-plate driving means and said linearly-movable-frame driving means in a predetermined sequence to thereby sample printed sheets through use of said sampling plate.

10. An apparatus for sampling a small number of printed sheets according to claim 9, further comprising printed-sheets braking means which is provided at a lower position of said opening portion in order to receive the tail end portions of printed sheets when the printed sheets are captured at their leading ends by the capture portion of said sampling plate and taken out through said opening portion.

11. An apparatus for sampling a small number of printed sheets according to claim 10, wherein said linearly movable frame comprises advancement-depth-into-printed-sheets-line adjustment means for adjusting the temporarily stopping position of said sampling plate in the moving direction of said sampling plate in the portion of the conveyance path zone corresponding to said opening portion.

12. An apparatus for sampling a small number of printed sheets according to claim 11, further comprising a predetermined-number-of-printed-sheets counter for causing said sampling control means to start said sampling-plate driving means and said linearly-movable-frame driving means for each conveyance of a predetermined number of printed sheets.

13. An apparatus for sampling a small number of printed sheets according to claim 10, further comprising a predetermined-number-of-printed-sheets counter for causing said sampling control means to start said sampling-plate driving means and said linearly-movable-frame driving means for each conveyance of a predetermined number of printed sheets.

14. An apparatus for sampling a small number of printed sheets according to claim 9, further comprising a predetermined-number-of-printed-sheets counter for causing said sampling control means to start said sampling-plate driving means and said linearly-movable-frame driving means for each conveyance of a predetermined number of printed sheets.

15. An apparatus for sampling a small number of printed sheets according to claim 14, further comprising a predetermined-number-of-printed-sheets counter for causing said sampling control means to start said sampling-plate driving means and said linearly-movable-frame driving means for each conveyance of a predetermined number of printed sheets.

16. An apparatus for sampling a small number of printed sheets according to claim 9, wherein said linearly movable frame comprises advancement-depth-into-printed-sheets-line adjustment means for adjusting the temporarily stopping position of said sampling plate in the moving direction of said sampling plate in the portion of the conveyance path zone corresponding to said opening portion.

* * * * *